(12) United States Patent
Adamo et al.

(10) Patent No.: US 8,999,391 B2
(45) Date of Patent: Apr. 7, 2015

(54) METHYL ETHYL HYDROXYETHYL CELLULOSE FOR PERSONAL CARE APPLICATIONS

(75) Inventors: Anthony John Adamo, Mountainside, NJ (US); Jaime Dion Hamm, Hillsborough, NJ (US); Mojahedul Islam, White House Station, NJ (US); Karen Lee White, Bridgewater, NJ (US); Samuel Anthony Vona, Jr., Highland, NY (US)

(73) Assignee: AKZO Nobel Chemicals International B.V., Amersfoort (NL)

(*) Notice: Subject to any disclaimer, the term of this patent is extended or adjusted under 35 U.S.C. 154(b) by 0 days.

(21) Appl. No.: 13/994,395

(22) PCT Filed: Dec. 14, 2011

(86) PCT No.: PCT/EP2011/072700
§ 371 (c)(1),
(2), (4) Date: Jun. 14, 2013

(87) PCT Pub. No.: WO2012/080301
PCT Pub. Date: Jun. 21, 2012

(65) Prior Publication Data
US 2013/0259818 A1    Oct. 3, 2013

Related U.S. Application Data

(60) Provisional application No. 61/424,264, filed on Dec. 17, 2010, provisional application No. 61/432,822, filed on Jan. 14, 2011, provisional application No. 61/466,242, filed on Mar. 22, 2011.

(30) Foreign Application Priority Data

Mar. 17, 2011 (EP) .................... 11158597

(51) Int. Cl.
  A61K 8/73     (2006.01)
  A61Q 5/02     (2006.01)
  (Continued)

(52) U.S. Cl.
  CPC . *A61K 8/731* (2013.01); *A61Q 5/02* (2013.01); *A61Q 5/06* (2013.01); *A61Q 17/005* (2013.01)

(58) Field of Classification Search
  None
  See application file for complete search history.

(56) References Cited

U.S. PATENT DOCUMENTS 3,472,840 A   10/1969   Stone et al.
4,940,785 A    7/1990   Stober et al.
(Continued)

FOREIGN PATENT DOCUMENTS

EP     1781248 B1    12/2010
JP   2000-44440 A     2/2000
(Continued)

OTHER PUBLICATIONS

English Abstract of JP2000044440, Feb. 15, 2000.
(Continued)

*Primary Examiner* — Anand Desai
*Assistant Examiner* — Melissa Mercier
(74) *Attorney, Agent, or Firm* — Sandra B. Weiss

(57) ABSTRACT

A thickening system for personal care formulations including methyl ethyl hydroxyethyl cellulose provides efficient thickening power in applications areas such as shampoo and styling gels. In addition to providing thickening, the methyl ethyl hydroxyethyl cellulose derived polymers also provide foam stability to shampoos and improved high humidity curl retention to hair gel compositions.

23 Claims, 9 Drawing Sheets

Plot of FDT vs. Concentration

(51) Int. Cl.
*A61Q 5/06* (2006.01)
*A61Q 17/00* (2006.01)

(56) References Cited

U.S. PATENT DOCUMENTS

| | | | | |
|---|---|---|---|---|
| 5,211,941 | A | * | 5/1993 | Komori et al. ............. 424/70.12 |
| 7,319,146 | B2 | * | 1/2008 | Bostrom et al ................. 536/91 |
| 2001/0022967 | A1 | | 9/2001 | Brandt et al. |
| 2009/0074697 | A1 | | 3/2009 | Huynh |
| 2011/0139170 | A1 | | 6/2011 | Hippe et al. |

FOREIGN PATENT DOCUMENTS

| WO | WO98/20854 A1 | 5/1998 |
|---|---|---|
| WO | WO98/31340 A1 | 7/1998 |
| WO | WO99/66888 A1 | 12/1999 |
| WO | WO02/078661 A2 | 10/2002 |
| WO | WO02/100360 A1 | 12/2002 |
| WO | WO03/048070 A1 | 6/2003 |
| WO | WO2006/045364 A1 | 5/2006 |
| WO | WO2007/127494 A2 | 11/2007 |
| WO | WO2010/020516 A1 | 2/2010 |

OTHER PUBLICATIONS

Ken Klein, "Evaluating Shampoo Foam", Cosmetics & Toiletries, vol. 119., No. 10, pp. 32-35, 2004.
Bermocoll in Construction Industry, Jan. 1, 2008, pp. 1-26.
Methocel Cellulose Ethers, Aug. 1, 2005, pp. 1-32.
European Patent Application No. 11158597.2 Search Report mailed Feb. 10, 2012.

* cited by examiner

METHYL ETHYL HYDROXYETHYL CELLULOSE FOR PERSONAL CARE APPLICATIONS

This application is a National Phase Application of PCT Application No. PCT/EP2011/072700, filed Dec. 14, 2011, and claims the benefit of priority to U.S. Provisional Patent Application Nos. 61/424,264, filed Dec. 17, 2010, 61/432,822, filed Jan. 14, 2011 and 61/466,242, filed Mar. 22, 2011 and EP Application No. 11158597.2, filed Mar. 17, 2011. Each of these applications is hereby incorporated by reference in its entirety herein.

FIELD OF INVENTION

The present invention relates to thickening agents comprising methyl ethyl hydroxyethyl cellulose in personal care applications.

BACKGROUND

Effective thickeners for use in personal care applications that also provide additional benefits to the formulator are in continuing demand. Of particularly interest is an effective thickener that is non-ionic so as to be compatible in conventional personal care formulations, particularly since many such formulations typically include cross-linked and neutralized polyacrylic acid.

Nonionic cellulose ethers have been known to be used as thickening agents in aqueous paint compositions, for instance in latex-containing paint compositions for providing stability, consistency and water retention to the aqueous paint compositions. Furthermore, nonionic cellulose ethers readily combine with frequently occurring ingredients in the paint compositions.

One nonionic cellulose ether often used in aqueous paint compositions is hydroxyethyl cellulose ethers which lacking a flocculation temperature below 100° C. in water. Such cellulose ethers are desirable since they normally, when used in aqueous paint compositions, contribute to a stable viscosity, a low tendency to flocculate organic and inorganic pigments and have a low tendency to form stable foams. However, the conventional hydroxyethyl cellulose ethers have the disadvantage of a comparatively weak thickening effect and little or no wetting ability.

Accordingly, there is a need for a thickener that is not only non-ionic and that offers effective thickening for a variety of personal care formulation areas, but also one that is naturally derived for improved biodegradability and sustainability.

SUMMARY OF THE INVENTION

Accordingly, the present invention relates to a personal care formulation comprising methyl ethyl hydroxyethyl cellulose and at least one at least one cosmetically acceptable ingredient. The methyl ethyl hydroxyethyl cellulose has a methyl DS to ethyl DS ratio of from about 1 to about 6.5. In embodiments of the invention, the personal care formulation may be a hair care formulation, a styling formulation or a hand sanitizer.

BRIEF DESCRIPTION OF THE DRAWING

The invention is best understood from the following detailed description when read in connection with the accompanying drawings. Included in the drawings are the following figures.

DETAILED DESCRIPTION OF THE INVENTION

Figure 1:
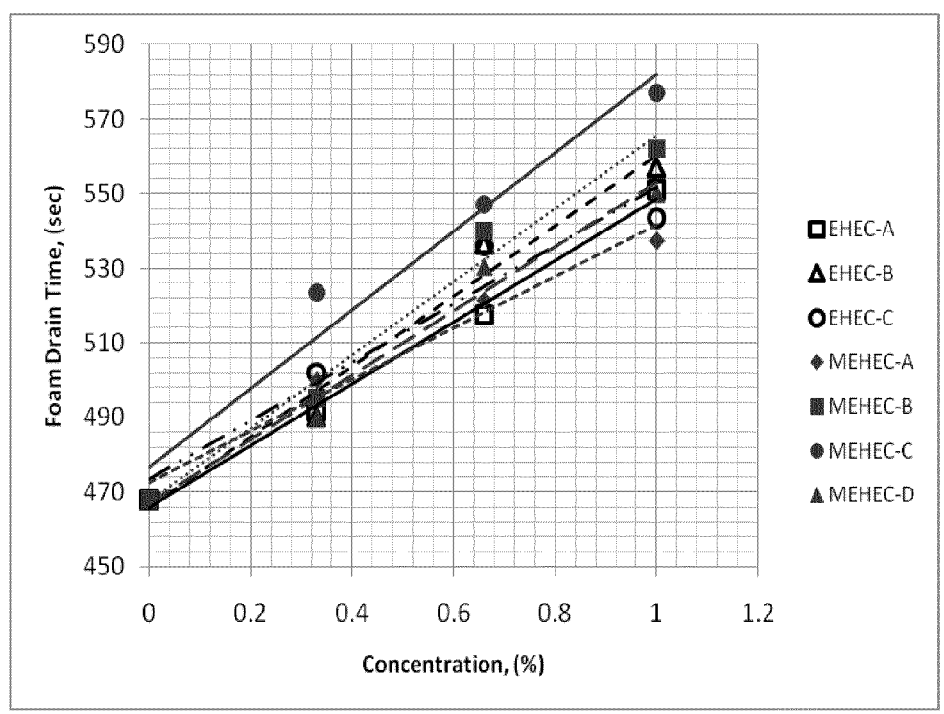
FIG. 1 is a chart including a plot of Foam Drain Time vs. Concentration for various cellulose ethers identified in Table 3A hereinbelow.

The present invention relates to the use of methyl ethyl hydroxyethyl cellulose (MEHEC) as a thickening agent for personal care formulations, such as hair care and styling formulations and hand sanitizers, in which improved thickening and texture and enhanced foam stability, foam creaminess, efficiency and high humidity curl retention can be achieved.

Methyl ethyl hydroxyethyl cellulose ethers can be prepared according to conventional methods that are known to those of ordinary skill in the art. For example, alkali cellulose (activated cellulose) may be prepared in one or several steps by mercerizing cellulose with alkali, in which the alkali cellulose is further reacted in one or several steps with appropriate amounts of ethylene oxide, methyl chloride and ethyl chloride in the presence of an organic reaction medium, for instance ethyl chloride, acetone, alkyl-blocked mono or poly(ethylene glycols), isopropanol, tert butanol or dimethoxyethane or mixtures thereof at a temperature in the range of from about 50 to about 120° C.

In an embodiment of the invention, the cellulose is mercerized in one or several steps with aqueous alkali in a total amount of about 0.8 to about 1.8 moles of alkali per mole of saccharide unit; and ethylene oxide in a total amount of about 2.6 to about 5.5 moles per mole of saccharide unit, methyl chloride in a total amount of about 0.2 to about 1.5 moles per mole of saccharide unit and ethyl chloride in a total amount of about 0.2 to about 1.5 moles per mole of saccharide unit. These components are added to and reacted with the mercerized cellulose in one or several steps in the presence of an organic reaction medium at a temperature from about 50 to about 120° C. In an embodiment of the invention, the weight ratio between the reaction medium and the cellulose can be about 1:1 to about 10:1, and in another embodiment from about 4:3 to about 3:1.

If ethyl chloride is used as a reaction medium, the desired amount of ethyl chloride is already present in the reaction mixture and there is no need for further addition of ethyl chloride. The ethylation can be regulated by the amount of alkali used, the reaction temperature and reaction time. If desired, a part of the alkali may be added at a later stage during the reaction in order to further activate the cellulose.

The total degree of substitution of methyl and ethyl can be controlled by the amount of alkali used in the mercerization process, since a corresponding equivalent amount of NaOH is consumed and forms sodium chloride. However, due to side reactions the yield of alkyl substitutions is about 40 to about 60%. U.S. Pat. No. 7,319,146, which is incorporated by reference in its entirety herein, provides a general description of the methods used in making MEHEC polymers.

The MEHEC thickeners of the present invention provide sustainable and naturally derived alternatives to synthetic polymers for personal care applications. The thickeners utilize cellulose as the polymer backbone and are modified so as to contain side chains of hydroxyethyl groups. The derivatization of the MEHEC is accomplished by treating the starting cellulose with ethylene oxide under alkaline conditions. The reaction of ethylene oxide with cellulose occurs with one of the glucose residue hydroxyls and in turn produces a new hydroxyl from the ring opening reaction of the ethylene oxide. Therefore, as the reaction continues, further substitution can occur directly on the glucose residue or at the terminal hydroxyl for a previously reacted ethylene oxide moiety. For this reason the level of ethylene oxide reacted with the cellulose is referred to as molar substitution (MS).

The hydroxyethyl cellulose is further treated with an ethylating agent under alkaline reaction conditions and then subsequently with a methylating agent. Since both of these alkylating steps react with the hydroxyl groups of the polymer and do not create any new hydroxyl groups in the process (unlike the reaction with ethylene oxide) the level of substitution of the polymer with these alkylating agents is referred to as degree of substitution (DS). For clarity, the methyl DS refers to the level of substitution of the methyl group, whereas the ethyl DS refers to the level of the ethyl substitution. In addition to the level of methyl DS and ethyl DS, the ratio of methyl DS to ethyl DS is a factor in considering the performance of the thickener. In an embodiment of the invention, the ratio of methyl DS to ethyl DS is from about 1.0 to about 6.5. In another embodiment the ratio of methyl DS to ethyl DS is from about 1.5 to about 3.0.

Another factor in the consideration of the MEHEC cellulosic thickeners of the invention is the molecular weight of the substituted polymer. Molecular weight can be determined by physical properties such as intrinsic viscosity or by spectrophotometeric analysis such as light scattering. For purposes of this invention, all molecular weights are given in weight average molecular weight (Mw) as determined by light scattering methods. The units reported are in Daltons (Da). In an embodiment of this invention, the molecular weight of the MEHEC will be in the range of from about 100,000 to about 3,000,000 weight average molecular weight. In another embodiment, the molecular weight of the MEHEC is in the range of from about 500,000 to about 2,000,000 Daltons. In yet another embodiment the weight average molecular weight of the MEHEC will be about 1.3 million or greater. In another embodiment, the weight average molecular weight is from about 1.4 to about 1.9 million.

As a thickener in styling formulations, MEHEC can provide a significant increase in the curl retention of the styled hair. In comparison, conventional thickeners used in styling formulations typically do not add to the performance of such formulations in terms of humidity resistance.

In personal care formulations, such as hair styling formulations, high humidity curl retention is a measure of how well the styled hair will hold its shape under conditions of 90% relative humidity (RH) and 23° C. In an embodiment of the invention, the high humidity curl retention is from about 20 percent to about 50 percent greater than the HEC or EHEC control at 90% RH for 24 hours.

For purposes of this invention, the MEHEC thickeners are present in personal care applications in an amount of from about 0.05 to about 5.0 percent (dry weight basis of the total formulation). In another embodiment, the level present will be from about 0.1 to about 1.0 percent (dry weight basis).

When used in personal care formulations, such as hair care and styling formulations, for example styling gels, optional additional ingredients can be added to provide a variety of additional properties. Various other additives, such as active and functional ingredients, may be included in the personal care formulation as defined herein. These include, but are not limited to, emollients, humectants, thickening agents, surfactants, UV light inhibitors, fixative polymers, preservatives, pigments, dyes, colorants, alpha hydroxy acids, aesthetic enhancers such as starch, perfumes and fragrances, film formers (water proofing agents), antiseptics, antifungal, antimicrobial and other medicaments and solvents. Additionally, conditioning agents can be used in combination with MEHEC, for example, cationic guar gum, cationic hydroxyethyl cellulose, cationic synthetic polymers and cationic fatty amine derivatives. These blended materials help to provide more substantivity and effective conditioning properties in hair.

Some non-limiting examples of polymers that can used in conjunction with the methyl ethyl hydroxyethylcellulose of this invention are polyoxythylenated vinyl acetate/crotonic acid copolymers, vinyl acetate crotonic acid (90/10) copolymers, vinyl acetate/crotonic acid/vinyl neodecanoate terpolymers, N-octylacrylamide/methylacrylate/hydroxypropyl methacrylate/acrylic acid/tert-butylaminoethyl methacrylate copolymers, and methyl vinyl ether/maleic anhydride (50/50) copolymers monoesterified with butanol or ethanol, acrylic acid/ethyl acrylate/N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), corn starch modified, sodium polystyrene sulfonate, polyquaterniums such as polyquaternium-4, polyquaternium-7, polyquaternium-10, polyquaternium-11, polyquarternium-16, polyquaternium-28, polyquaternium-29, polyquaternium-46, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, PVP/dimethylaminoethylmethacrylate copolymer, PVP/DMAPA acrylates copolymer, PVP/vinylcaprolactam/DMAPA acrylates copolymer, vinyl caprolactam/PVP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, vinylpyrrolidone/vinyl acetate/vinyl propionate terpolymers, VA/crotonates, cationic and amphoteric guar, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer, methacrylates/acrylates copolymer/amine salt, polyvinylcaprolactam, polyurethanes, hydroxypropyl guar, hydroxypropyl guar hydroxypropyl trimmonium chloride, poly (methacrylic acid/acrylamidomethyl propane sulfonic acid, poylurethane/acrylate copolymers and hydroxypropyl trimmonium chloride guar, particularly acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), polyurethane, corn starch modified, sodium polystyrene sulfonate, polyquaternium-4, polyquarternium-10, and polyurethane/acrylates copolymer.

In addition to the cellulosic based polymer, the composition of this invention will include a cosmetically acceptable ingredient. The ingredient can be an emollient, fragrance, exfoliant, medicament, whitening agent, acne treatment agent, a preservative, vitamins, proteins, a cleanser or a conditioning agent.

Examples of cleansers suitable for use in the present invention include, but are not limited to, are sodium lauryl sulfate (SLS), sodium laureth sulfate (SLES), ammonium lauryl ether sulfate (ALES), alkanolamides, alkylaryl sulfonates, alkylaryl sulfonic acids, alkylbenzenes, amine acetates, amine oxides, amines, sulfonated amines and amides, betaines, block polymers, carboxylated alcohol or alkylphenol ethoxylates, diphenyl sulfonate derivatives, ethoxylated alcohols, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, olefin sulfonates, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, silicone-based surfactants, soaps, sorbitan derivative, sucrose and glucose esters and derivatives, sulfates and sulfonates of oils and fatty acids, sulfates and sulfonates ethoxylated alkyl phenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum, sulfosuccinamates, sulfosuccinates and derivatives.

Preservatives are often used in personal care formulations to provide long term shelf stability. These can be selected from among methylparaben, propylparaben, butylparaben, DMDM hydantoin, imidazolidinyl urea, gluteraldehyde, phenoxyethanol, benzalkonium chloride, methane ammonium chloride, benzethonium chloride, benzyl alcohol, chlorobenzyl alcohol, methylchloroisothiazolinone, methylisothiazolinone, sodium benzoate, chloracetamide, triclosan, iodopropynyl butylcarbamate, sodium pyrithione, and zinc pyrithione.

In another embodiment, the MEHEC thickeners may be used in alcohol based hand sanitizers. The use of MEHEC thickeners in alcohol based hand sanitizers can provide an effective material which provides benefits, such as less tack, lower use level and smoother feel, to the user. The MEHEC thickeners of this invention have a weight average molecular weight from about 1.5 to about 2.0 million (Daltons) and will have a methyl DS to ethyl DS ratio of from about 1.0 to about 6.5. In an embodiment of this invention, the MEHEC thickeners may be present in the formulation in an amount of from about 0.1 to about 2.0 percent (based on dry weight of the total hydro-alcoholic formulation) and is soluble in ethanol or isopropanol or ethanol/isopropanol water blends, wherein the alcohol in the blend is greater than about 60%.

When used in hair care formulations, such as shampoos, the MEHEC thickener of the present invention can function to provide better foam stability and foam density of the surfactant system. Foam quality is desirable as the user perceives the creaminess of the foam as a sign of luxury and high quality. As compared to known foam stabilizers, any increase in foam stability is generally difficult to obtain and may even be difficult to quantify. Small increases in foam stability, which can be measured based on foam density or drain time (as described below) are desirable and relate to a significant sensual enhancement that is otherwise difficult to measure instrumentally. In an embodiment of the invention, the MEHEC thickeners of the invention have a foam drainage time (FDT) of from about 540 sec. to about 580 sec., as measured by the foam drainage test, as described herein below. In another embodiment, the FDT is from about 560 sec. to about 580 sec.

In shampoo formulations, the molecular weight and ratio of methyl DS to ethyl DS is important. In an embodiment, the ratio is from about 1.0 to about 6.5. In another embodiment, the ratio of methyl DS to ethyl DS is from about 1.25 to about 3.0. For this application, the weight average molecular weight is from about 1.6 to about 2.0 million (Daltons). In another embodiment of this invention the weight average molecular weight is from about 1.7 to about 1.9 million (Daltons).

The MEHEC polymers of this invention provide good compatibility with all types of surfactants and a wide range of salt and pH concentrations. This affords more flexibility in the type of materials that can be used as well as an extended range of viscosities not typically available with other polymeric thickeners.

In an embodiment of this invention, particularly where the hair formulation is a shampoo, the formulation contains a sulfate free surfactant and MEHEC. Examples of sulfate free surfactants include, but are not limited to, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, silicone-based surfactants, alpha-olefin sulfonate, alkylaryl sulfonates, sulfonates of oils and fatty acids, sulfonates of ethoxylated alkyl phenols, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum and derivatives thereof. In an embodiment of the invention, the sulfate free surfactants are sulfonates or ethoxylates.

In another embodiment the formulation contains sulfated surfactants. Some non-limiting examples of sulfated surfactants are sodium lauryl sulfate (SLS), sodium laureth sulfate (SLES), alkanolamides, alkylaryl sulfonic acids, sulfates of oils and fatty acids, sulfates of ethoxylated alkyl phenols, sulfates of alcohols, sulfates of ethoxylated alcohols, sulfates of fatty esters, sulfosuccinamates, sulfosuccinates and derivatives thereof.

In yet another embodiment the formulation contains MEHEC and salt, such as sodium chloride or potassium chloride. Since, MEHEC is a non-ionic polymer it has considerable tolerance to salts. This benefit allows MEHEC to be utilized in a variety of personal care applications.

There are many tests used for traditional foam evaluation, including Ross Miles, Cylinder shake, perforated disk, Moldavanyi-Hunger bubbler, Hart-deGeorge blender method and the blender foam volume density test. For a general review of shampoo foam quality and stability see K. Klein, "Evaluating Shampoo Foam", Cosmetics & Toiletries, V. 119, No 10, Pages 32-35, 2004, which is incorporated by reference in its entirety herein. For purposes of this invention, the foam test described below (see experimental section) was a modification of the blender foam volume/density test.

In addition to the MEHEC thickening polymer, shampoo compositions may optionally include other ingredients. Some non-limiting examples of these ingredients include, but are not limited to, conditioning agents such as silicone oils, either volatile or non-volatile, natural and synthetic oils. Suitable silicone oils that can be added to the compositions include dimethicone, dimethiconol, polydimethylsiloxane, silicone oils with various DC fluid ranges from Dow Corning. Suitable natural oils, such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate can also be used. Some examples of non-ionic conditioning agents are polyols such as glycerin, glycol and derivatives, polyethyleneglycols, which may be known by the trade names Carbowax® PEG from Union Carbide and Polyox® WSR range from Amerchol, polyglycerin, polyethyleneglycol mono- or di-fatty acid esters.

Suitable cationic polymers that may be used in the formulation are those of best known with their CTFA category name Polyquaternium. Some examples of this class of polymer are Polyquaternium 6, Polyquaternium 7, Polyquaternium 10, Polyquaternium 11, Polyquaternium 16, Polyquaternium 22 and Polyquaternium 28, Polyquaternium 4, Polyquaternium 37, Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Naturally derived cellulose type polymers known as Polymer JR® type from Amerchol, Polyquaternium 10 or cationic guar gum known with trade name Jaguar® from Rhone-Poulenc, and Guar hydroxypropyl trimonium chloride, chitosan and chitin can also be included in the personal care formulations as cationic natural polymers may also optionally be included with the inventive MEHEC thickeners.

MEHEC is a natural based polymer with unique properties, such as high surface activity, wide molecular weight range and various degree of ethoxylation, degree of alkylation, and alkyl group size. These properties contribute to enhanced foam characteristics, particularly for personal care applications, including rinse off applications such as shampoos, body washes and facial cleansers. Also, MEHEC builds viscosity, exhibits shear thinning rheology, improved elasticity, formula stabilization and salt tolerance attributes that are desirable for a variety of personal care applications including shampoos, body washes, conditioners and hair styling formulations.

The present invention will now be illustrated by the following examples. The examples are intended to exemplify the present invention but are not intended to limit the scope of the invention in any way. The breadth and scope of the invention are to be limited solely by the claims appended hereto.

EXPERIMENTAL

Example 1

Cellulosic Ether Properties

Various EHECs and MEHECs were tested in shampoo and hair styling formulations. Table 1 lists the cellulose ether samples together with their basic data. All molecular weights are expressed as weight average molecular weight (in Daltons). All viscosities reported have been measured at shear rate of $10\ s^{-1}$ and $1\ s^{-1}$ measured using a Rheometrics rheometer (Rheometric Scientific, Model # SR-5000) and at 25° C.

TABLE 1

Degree of substitution and basic properties of Cellulose ethers

| | Cellulosic polymer Structural Data | | | | | Viscosity | |
| --- | --- | --- | --- | --- | --- | --- | --- |
| Sample | $MS_{EO}$ | $DS_{Ethyl}$ | $DS_{Methyl}$ | DS ratio (methyl/ethyl) | $(MW)_{n\ millions}$ | $1\ s^{-1}$ mPa·s | $10\ s^{-1}$ mPa·s |
| EHEC-A | 2.35 | 0.95 | 0 | 0.00 | 1.68 | 5283 | 2122 |
| EHEC-B | 1.90 | 0.90 | 0 | 0.00 | 1.68 | 7567 | 2754 |
| EHEC-C | 2.70 | 0.85 | 0 | 0.00 | 1.76 | 5422 | 2029 |
| MEHEC-A | 1.70 | 0.45 | 0.45 | 1.00 | 1.58 | 8477 | 2925 |
| MEHEC-B | 2.45 | 0.45 | 0.55 | 1.22 | 1.82 | 9482 | 3199 |
| MEHEC-C | 1.10 | 0.30 | 0.75 | 2.50 | 1.48 | 10477 | 3798 |
| MEHEC-D | 0.30 | 0.20 | 1.25 | 6.25 | 1.21 | 8299 | 3016 |

Example 2

Sulfate Free Shampoo Formulations

These cellulose ethers detailed in the above Table 1 were tested in a sulfate-free shampoo formulation as shown and detailed in the table below (Table 2). The surfactant system of the samples below contained sodium cocoyl Isethionate, disodium laureth sulfosuccinate and decyl glucoside and the cellulosic material was added as a thickener and foam stabilizer.

TABLE 2

Sulfate free shampoo formulations

% Active (dry basis)
Formulation #

| Ingredients | A | B | C | D | E | F | G | H |
|---|---|---|---|---|---|---|---|---|
| Sodium Cocoyl Isethionate | 5 | 5 | 5 | 5 | 5 | 5 | 5 | 5 |
| Disodium Laureth Sulfosuccinate | 1.67 | 1.67 | 1.67 | 1.67 | 1.67 | 1.67 | 1.67 | 1.67 |
| Decyl Glucoside | 3.33 | 3.33 | 3.33 | 3.33 | 3.33 | 3.33 | 3.33 | 3.33 |
| EHEC-A | | 1 | | | | | | |
| EHEC-B | | | 1 | | | | | |
| EHEC-C | | | | 1 | | | | |
| MEHEC-A | | | | | 1 | | | |
| MEHEC-B | | | | | | 1 | | |
| MEHEC-C | | | | | | | 1 | |
| MEHEC-D | | | | | | | | 1 |
| Water | 90 | 89 | 89 | 89 | 89 | 89 | 89 | 89 |
| Total | 100 | 100 | 100 | 100 | 100 | 100 | 100 | 100 |

Example 3

Foam Property Evaluation (Foam Drain Time, FDT)

The Foam property was evaluated by creating a foam using a blender and the measuring the time taken for half of total liquid to drain from the foam matrix, according to the procedure below.

Procedure:

Prepare a 1% solution of each of the formulations listed in table 1, above by diluting with water. A total of 200 ml of the 1% solution was transferred to a blender (Oster Fusion, 3 speed blender). Blend the solution at medium speed for 30 sec. Transfer the resulting foam quickly into a 1000 ml cylinder, ensuring that as much of foam as possible is transferred. Observe as the liquid from the foam matrix drains to the bottom of the cylinder. Note the time ($t_{1/2}$) when the volume reaches 100 ml. The drain time is calculated by subtracting 30 sec from $t_{112}$ (FDT=$t_{1/2}$−30).

TABLE 3

Foam Quality

| Formulation # | EHEC or MEHEC | FDT (sec) |
|---|---|---|
| A | No polymer | 468 |
| B | EHEC-A | 551 |
| C | EHEC-B | 557 |
| D | EHEC-C | 544 |
| E | MEHEC-A | 538 |
| F | MEHEC-B | 562 |
| G | MEHEC-C | 577 |
| H | MEHEC-D | 550 |

The results shown in Table 3 demonstrate the MEHECs with a range of methyl DS to ethyl DS ratio of about 1.2 to about 3.0 provides an enhanced foam stability as measured by the "foam drainage time".

TABLE 3A

Effect of polymer concentration on Foam Drain time (FDT)

| Polymer Conc. % | EHEC-A | EHEC-B | EHEC-C | MEHEC-A | MEHEC-B | MEHEC-C | MEHEC-D |
|---|---|---|---|---|---|---|---|
| 1 | 551 | 557 | 544 | 538 | 562 | 577 | 550 |
| 0.66 | 518 | 537 | 536 | 522 | 540 | 547 | 531 |
| 0.33 | 492 | 490 | 502 | 500 | 495 | 524 | 490 |
| 0 | 468 | 468 | 468 | 468 | 468 | 468 | 468 |

The results in Table 3A are shown graphically below in FIG. 1. The importance of this test can be seen the in relationship between the concentration of the polymer and the increase in the Foam Drain time. For example, to provide the performance of EHEC-A at 0.66% polymer concentration, one would only need 0.33% of MEHEC-C (½ the concentration) to achieve the same FDT results.

Example 4

Hair Gel Formulations

Hair gels were also prepared using some of the cellulose ethers listed in Table 1 above. Table 4 below lists formulations prepared and studied. The samples were prepared in the following manner. A total of 2.0 g of MEHEC and 3.0 g of PVP were mixed together and then added to 95.0 g of water under adequate shear with an overhead mixer (400 rpm). The solution was continued to mix until fully dissolved and complete build-up of viscosity (visually evaluation). For some of the products hydration was much faster, for those instances the powders were mixed at a higher mixing speed of 700-800 rpm.

TABLE 4

Hair Gel formulation containing various cellulose ethers

| | % Active Formulation # | | | | |
|---|---|---|---|---|---|
| Ingredients | I | J | K | L | M |
| EHEC-A | 2 | | | | |
| EHEC-B | | 2 | | | |
| EHEC-C | | | 2 | | |
| MEHEC-A | | | | 2 | |
| MEHEC-C | | | | | 2 |
| PVP K90 | 3 | 3 | 3 | 3 | 3 |
| Water | 95 | 95 | 95 | 95 | 95 |
| Total | 100 | 100 | 100 | 100 | 100 |

Example 5

High Humidity Curl Retention Test

Evaluation was performed on 10" long×2-gram swatches of European virgin brown hair (9 replicate swatches per sample). Curl retention testing was run in a humidity chamber set at 21° C./90% Relative Humidity for a total of 24 hours. Measurements for % Curl retention were read and calculated at various time intervals (1, 5 and 24 hours).

Procedure:

The hair swatch was wetted with water and combed through to remove tangles and squeeze out excess water (run swatch between thumb and index finger). A total of 0.5 g of sample was applied to each swatch, and gently worked into the swatch by hand and combed through. The swatch was rolled onto a ½" diameter Teflon mandrel. Then carefully remove the rolled swatch from the mandrel and secure with two hair clips. The curls were placed on a tray and dried in an oven overnight at 120° C. The dried curls were removed from the oven and allowed to cool to room temperature. The curls were suspended from the bound end of swatch, on a graduated clear, transparent curl retention board. The clips were removed from the curls and allowed to gently unwind from the glass rod.

The initial curl length was measured before placing the boards and curls into environmental chamber (21 C, 90% relative humidity). Curl lengths were recorded at 15, 30, 60, 90 minutes, 2 hour, 3, 4, 5 and 24 hour time intervals. Percent % Curl Retention was calculated by dividing the length of the swatch at T=0 (initial curl length) by the length of the curl at the specified time (at temperature and humidity) for each sample.

TABLE 5

High Humidity Curl Retention (%) at 90% RH and 21° C.

| | | % Curl retention at time, hrs | |
|---|---|---|---|
| Formulation # | Sample | 5 | 24 |
| I | EHEC-A | 24 | 23 |
| J | EHEC-B | 25 | 24 |
| K | EHEC-C | 26 | 23 |
| L | MEHEC-A | 26 | 23 |
| M | MEHEC-B | 35 | 29 |

The results shown in Table 5 demonstrate that MEHEC with a molecular weight of about 1.5 million and a methyl DS to ethyl DS of about 2.5 (formulation M) gave the highest percent of high humidity curl retention as compared to the EHEC polymers (formulations I to K) and even to a MEHEC with a higher molecular weight, but lower methyl DS to ethyl DS ratio (formulation L). Alternatively stated, it is the ratio of methyl DS to ethyl DS that surprisingly provides the increase in high humidity curl retention and not necessary the molecular weight of the polymer. By providing the increased humidity resistance without the increase in molecular weight means the viscosity of the solution can be lower at the same concentration.

Example 6

Viscosity Evaluation

As known to those of ordinary skill in the art, rheological properties are of great importance in many personal care applications where the flow behavior is most desirable, for example: shampoo, conditioner and hair gel formulations.

TABLE 6

Comparison of Viscosity for Selected Surfactants

| Formula | wt % |
|---|---|
| Water | 89 |
| MEHEC-B % | 1 |
| SLES/ALES/AOS | 10 |
| Total | 100 |

| MEHEC-B (%) | SLES Viscosity (cps) | ALES | AOS |
|---|---|---|---|
| 0.25 | 36 | 100 | 20 |
| 0.5 | 570 | 810 | 200 |
| 1 | 1000 | 1290 | 810 |

Figure 2:
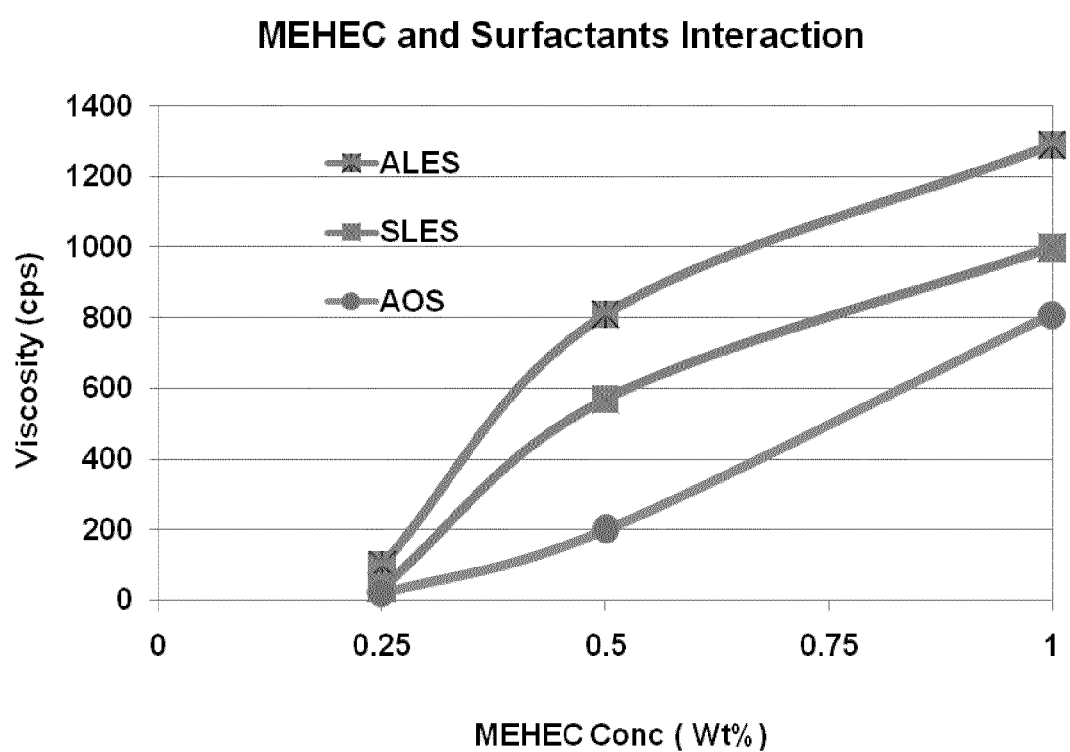
FIG. 2 is a chart illustrating showing the effect of MEHEC in combination with selected anionic surfactants on viscosity at various concentrations.

The results shown in Table 6 indicate that MEHEC provides significantly higher viscosity when used in conjunction with ALES or SLES. FIG. 2 illustrates these results, showing the various degrees of interactions of MEHEC with different types of anionic surfactant types, where the viscosity increases as the MEHEC concentration increases. (Viscosities were measured using a Brookfield viscometer (Spindle T-C at 10 rpm) and at room temp.)

Figure 3:
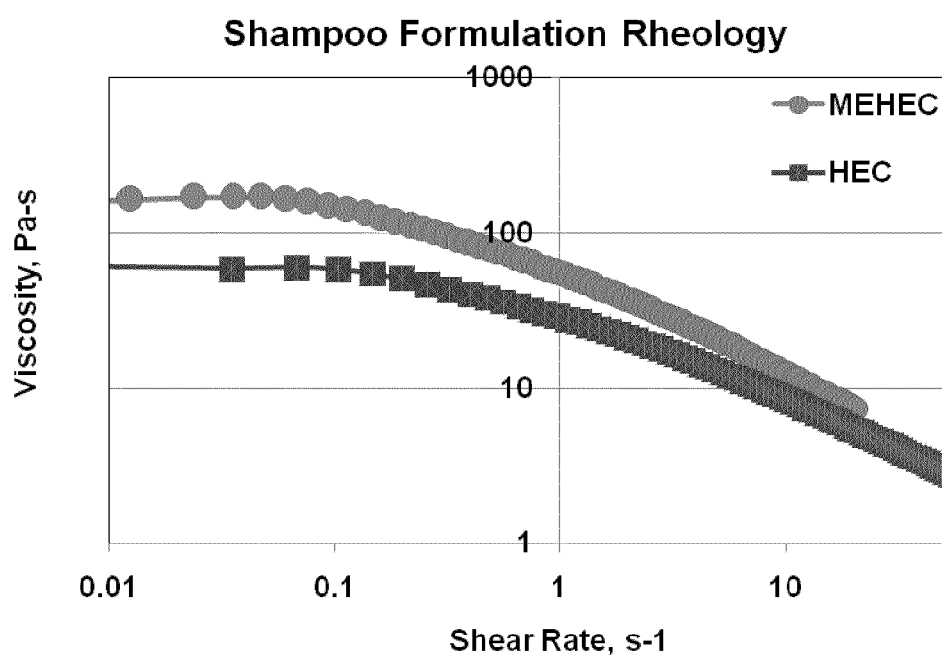
FIG. 3 is a chart of the viscosity and shear rate of a shampoo formulation including MEHEC compared to a shampoo formulation including HEC.
Figure 4:
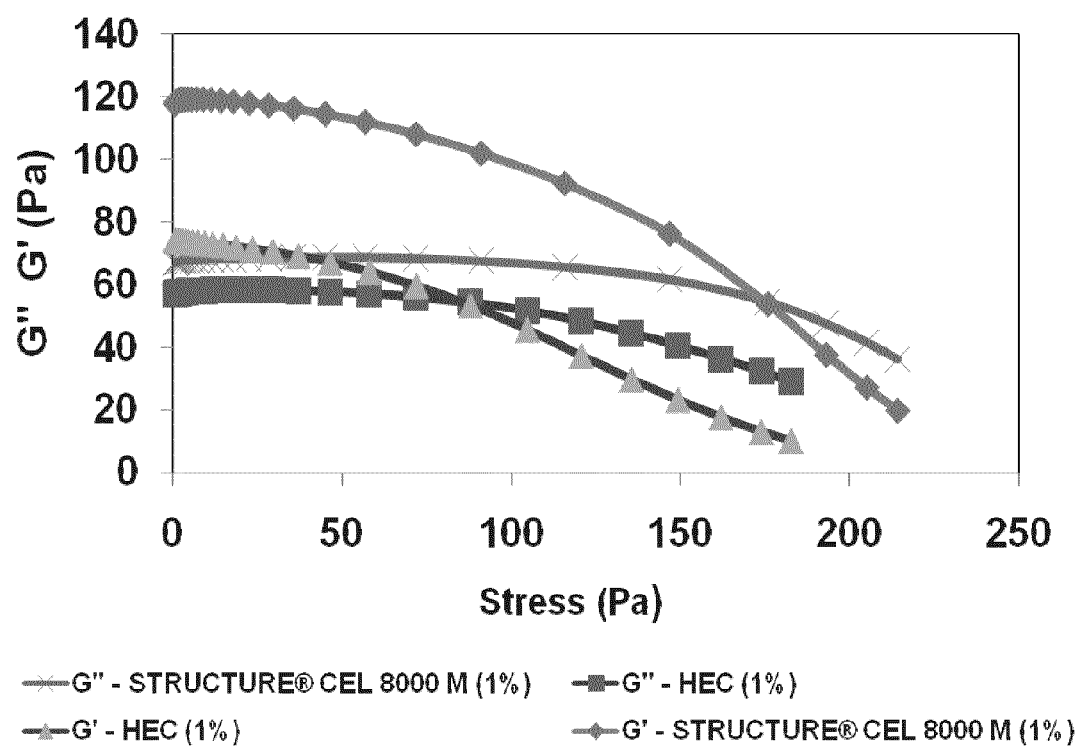
FIG. 4 is a chart showing the impact of MEHEC on shampoo formulation elasticity compared to HEC.

By way of comparison, FIG. 3 illustrates the viscosity of a shampoo formulation including MEHEC compared to a shampoo formulation including HEC. As shown, the viscosity of the shampoo formulation with MEHEC decreases with increasing shear rate and is more effective in building higher viscosity than HEC. Similarly, as shown in FIG. 4, MEHEC exhibits improved shampoo formulation elasticity compared to HEC.

Figure 5:
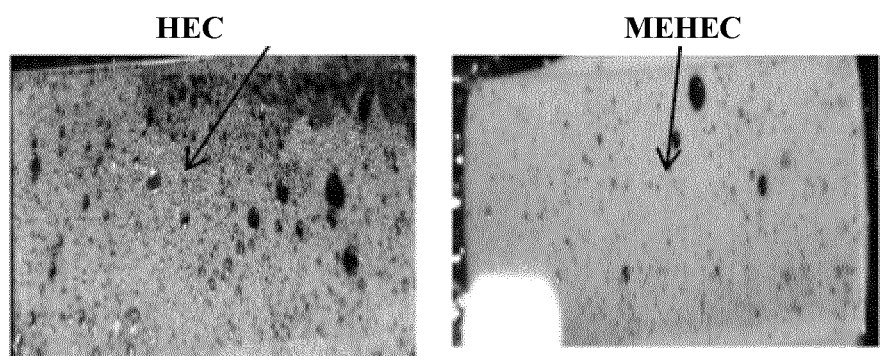
FIG. 5 is an image illustrating foam density of MEHEC vs. HEC.

In addition, as noted above, MEHEC exhibits a positive impact on the foam characteristics of shampoo formulations. Without wishing to be bound by theory, it is believed that by increasing the elasticity of the foam membrane due to interaction with surfactants prevents drainage and results in enhanced foam stability and drainage time, thus providing a shampoo with denser, creamier and luxurious foam. FIG. 5 shows comparative images of foam density of MEHEC vs. HEC. As shown, MEHEC exhibits reduced bubble size, foam quality, and enhanced creaminess compared to HEC when used in cleansing systems.

Figure 6:
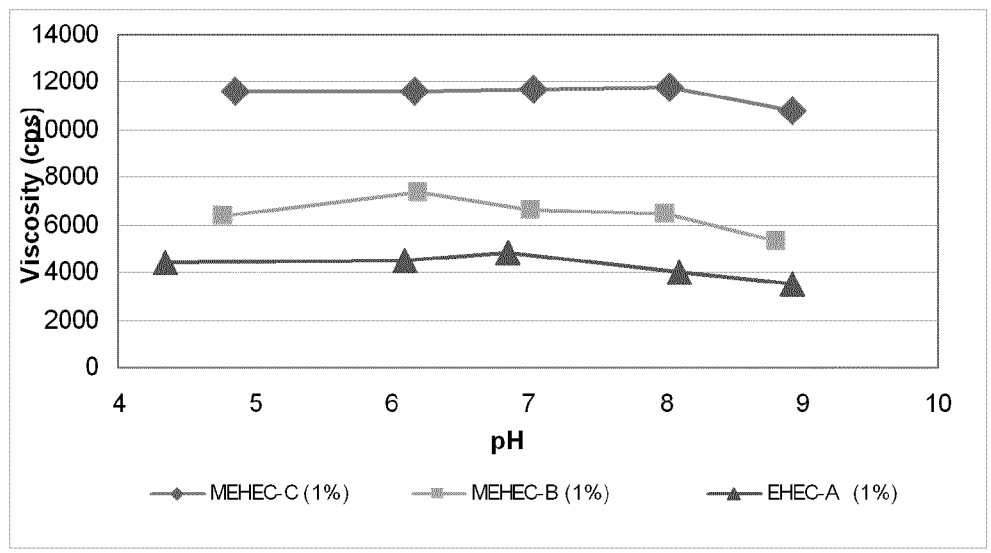
FIG. 6 is a chart comparing viscosities of MEHEC-B and MEHEC-C compared to a comparable EHEC, EHEC-A.

Table 7 comprises data showing that two embodiments of the MEHEC's have higher viscosity than EHEC. These are solutions of MEHEC's and EHEC surfactant in water. (Viscosities were measured using a Brookfield viscometer (Spindle T-C at 10 rpm) and at room temp.) The data from Table 7 are shown graphically in FIG. 6.

TABLE 7

| Product | pH final | Viscosity |
| --- | --- | --- |
| MEHEC-B (1%) | 4.77 | 6400 |
| MEHEC-B (1%) | 6.19 | 7400 |
| MEHEC-B (1%) | 7.02 | 6600 |
| MEHEC-B (1%) | 8.00 | 6500 |
| MEHEC-B (1%) | 8.81 | 5300 |
| MEHEC-C (1%) | 4.86 | 11600 |
| MEHEC-C (1%) | 6.16 | 11650 |
| MEHEC-C (1%) | 7.03 | 11700 |
| MEHEC-C (1%) | 8.04 | 11800 |
| MEHEC-C (1%) | 8.93 | 10800 |
| EHEC-A (1%) | 4.34 | 4400 |
| EHEC-A (1%) | 6.10 | 4500 |
| EHEC-A (1%) | 6.85 | 4800 |
| EHEC-A (1%) | 8.11 | 4000 |
| EHEC-A (1%) | 8.93 | 3500 |
| MEHEC-A (1%) | 4.6 | 4400 |
| MEHEC-A (1%) | 6.39 | 5400 |
| MEHEC-A (1%) | 7.08 | 4600 |
| MEHEC-A (1%) | 8.32 | 4500 |
| MEHEC-A (1%) | 9.02 | 3800 |

Table 7 shows that at similar molecular weight and substitution level, the MEHEC provides higher viscosity and less pH sensitivity than a corresponding EHEC. This will afford a broader range of formulation and/or a lower usage level to obtain the same viscosity of the personal care formulation.

Example 7

Evaluation of Interaction of MEHEC Compositions with Salt

Figure 7:
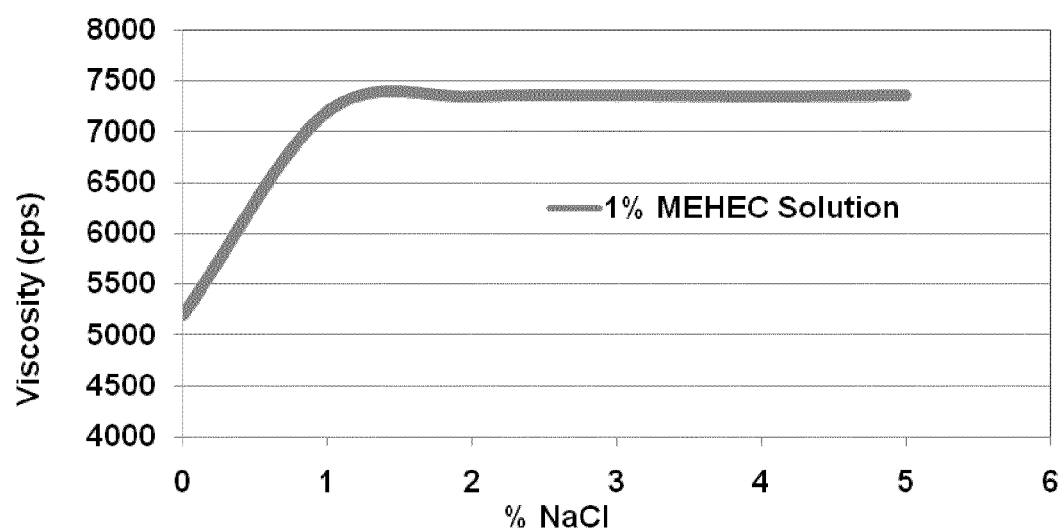
FIG. 7 is a chart showing a salt curve of a 1% MEHEC solution without surfactants.
Figure 8:
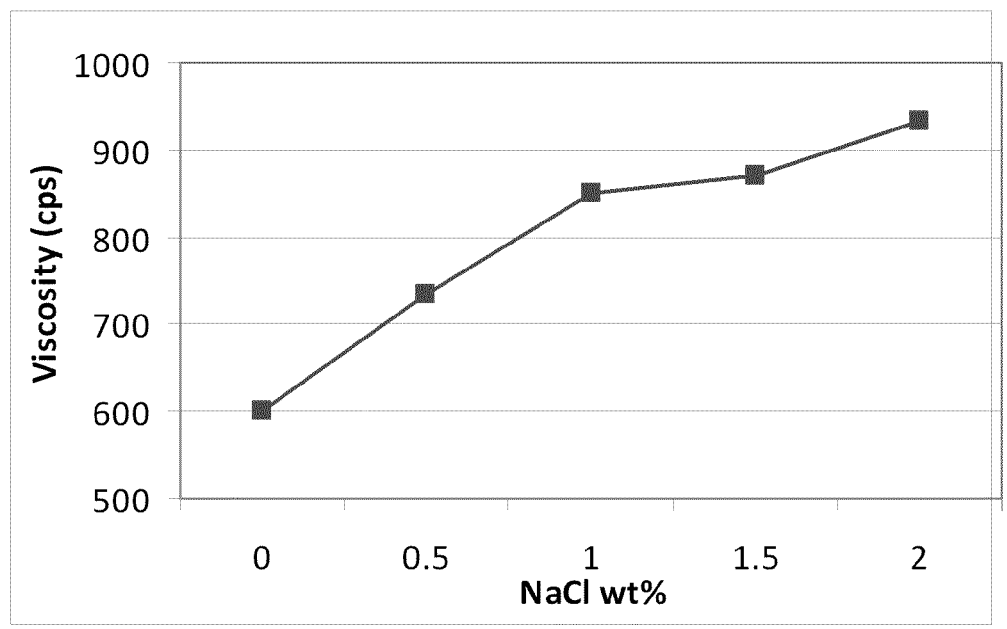
FIG. 8 is a chart showing a salt curve of a 1% MEHEC solution in combination with 10% of the anionic surfactant, alpha-olefin sulfonate (AOS).

FIG. 7 is a salt curve of a 1% MEHEC solution without surfactants. As shown in Table 8 and FIG. 8, MEHEC, when used in combination with the anionic surfactant alpha-olefin sulfonate (AOS), does not show any signs of incompatibility at the higher salt levels, as indicated by the data evidencing the clear appearance/clarity and increased viscosity. (Viscosities were measured using a Brookfield viscometer (Spindle T-C at 10 rpm) and at room temp.)

TABLE 8

1% MEHEC-B + 10% AOS

| Salt Level | Viscosity | Appearance |
| --- | --- | --- |
| 0 | 600 | Clear |
| 0.5 | 735 | Clear |
| 1 | 850 | Clear |
| 1.5 | 870 | Clear |
| 2 | 934 | Clear |

Figure 9:
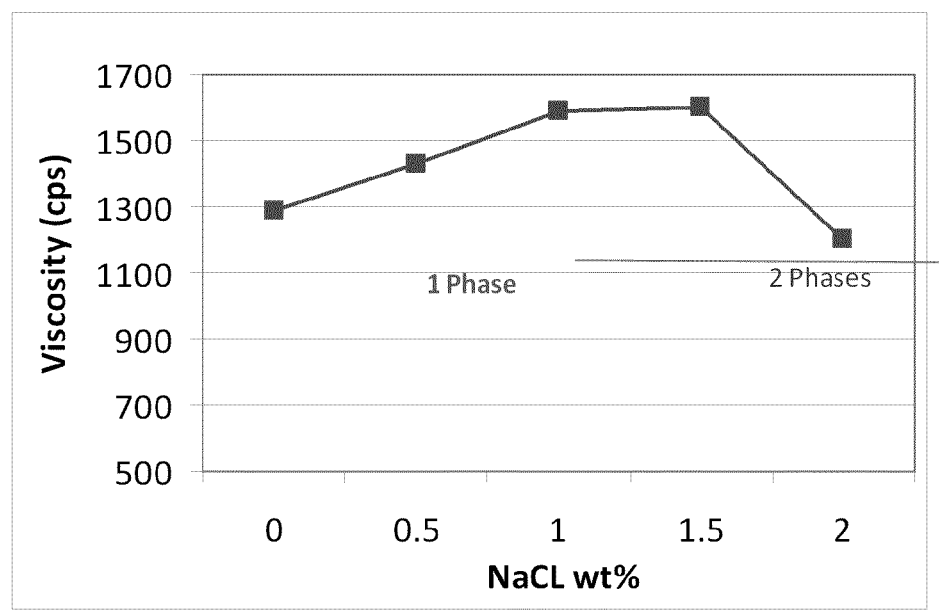
FIG. 9 is a chart showing a salt curve of a 1% MEHEC solution in combination with 10% of the anionic surfactant, sodium laureth sulfate (SLS).

Similarly, the MEHEC used in combination with SLES is also exhibits good salt compatibility at salt levels of up to about 1.5%. As shown, however, in Table 9 and in FIG. 9, at salt levels above about 1.5% the compatibility of the polymer and surfactant diminishes.

TABLE 9

1% MEHEC-B + 10% SLES

| Salt Level | Viscosity | Appearance |
| --- | --- | --- |
| 0 | 1290 | Clear |
| 0.5 | 1430 | Clear |
| 1 | 1590 | Clear |
| 1.5 | 1600 | Clear |
| 2 | 1200 | 2-Phase |

Example 8

Shampoo Formulation Evaluation

TABLE 10

Sulfate-containing Shampoo Formulation

| Ingredient | INCI Name | Active wt % | Active wt % |
| --- | --- | --- | --- |
| SLES | Sodium Laureth Sulfate | 3.75 | 3.75 |
| CAPB | Cocamidopropyl betaine | 1.5 | 1.5 |
| Glydant Plus | DMDM Hydantoin (and) Iodopropylnyl Butylcarbamate | 0.5 | 0.5 |
| MEHEC-B | Methyl Hydroxyethylcellulose | 1 | |
| EHEC-A | Ethyl Hydroxyethylcellulose | | 1 |
| Water | | q.s | q.s. |
| Viscosity (cps) | | 8300 | 4164 |

1. SLES = Standapol ® ES-2 (25% active) available from Cognis Corporation.
2. CAPB = Crodateric ™ CAB 30 (30% active) available from Croda, Inc.
3. Glydant Plus = Glydant ™ Plus (liquid) available from Lonza.

TABLE 11

Sulfate-Free Shampoo Formulation

| Ingredient | INCI Name | Active wt % | Active wt % |
| --- | --- | --- | --- |
| AOS | Sodium C14-C16 Olefin Sulfonate | 2.9 | 2.9 |
| CAPB | Cocamidopropyl betaine | 2.25 | 2.25 |
| Glydant Plus | DMDM Hydantoin (and) Iodopropylnyl Butylcarbamate | 0.5 | 0.5 |

TABLE 11-continued

Sulfate-Free Shampoo Formulation

| Ingredient | INCI Name | Active wt % | Active wt % |
|---|---|---|---|
| MEHEC-B | Methyl Hydroxyethylcellulose | 1 | |
| EHEC-A | Ethyl Hydroxyethylcellulose | | 1 |
| Water | | q.s. | q.s. |
| Viscosity (cps) | | 21100 | 16420 |

1. AOS = Witconate ™ AOS (39% active) available from Akzo Nobel Surface Chemistry.
2. CAPB = Crodateric ™ CAB 30 (30% active) available from Croda, Inc.
3. Glydant Plus = Glydant ™ Plus (liquid) available from Lonza.

As shown in each of the two examples of shampoo formulations, one sulfate-containing and the other being sulfate-free, the formulations including the MEHEC had significantly higher viscosities than the same formulations including EHEC having a comparable substitution and molecular weight (see Table 1). (Viscosities were measured using a Brookfield viscometer (Spindle T-C at 10 rpm) and at room temp.)

Example 9

Viscosity Stability of Polymer Solutions Containing MEHEC

Solutions of EHEC and MEHEC were prepared and the corresponding viscosities measured using the following procedure:

1. Solutions of both the EHEC (4400 E) and the MEHEC (8000 M) were prepared by dissolving 15.0 grams of polymer (dry basis) in 980 grams of deionized water and preserved with 5.0 Glydant™ Plus Liquid (preservative, available from Lonza Group Ltd, Basel, Switzerland). Each master batch was adjusted to pH 7 using 25% NaOH as needed.
2. 66.7 grams of each polymer solution was poured off into six 100 gram jars and adjusted to one of the following pH points: 2, 3, 4, 9, 10 and 11 using either 25% NaOH or 20% Citric Acid. Water was added to QS to a total sample weight of 100 g. The pH 7 samples were diluted with water to give a concentration of 1.00% active polymer.
3. Initial viscosities were measured using a Brookfield RV/DV I Prime viscometer with a T-C heliopath spindle at 10 rpm for 2 minutes. Each sample was then placed in a 45° C. oven for one week. After one week the viscosities were measured again.

TABLE 12

Viscosity stability of polymer solutions at various pHs.

| pH | 8000M initial | 8000M 1 wk @ 45° C. | % Loss | 4400 E initial | 4400 E 1 wk @ 45° C. | % Loss |
|---|---|---|---|---|---|---|
| 2 | 6240 | 100 | 98.40 | 4060 | 100 | 97.54 |
| 3 | 6040 | 3080 | 49.01 | 3980 | 1440 | 63.82 |
| 4 | 5840 | 5020 | 14.04 | 4080 | 2520 | 38.24 |
| 7 | 5620 | 6460 | −14.95 | 4040 | 4260 | −5.45 |
| 9 | 5860 | 6300 | −7.51 | 4360 | 4380 | −0.46 |
| 10 | 5520 | 5660 | −2.54 | 4180 | 2960 | 29.19 |
| 11 | 5340 | 3320 | 37.83 | 4120 | 400 | 90.29 |

This data suggests that solutions of MEHEC are much more tolerant, in terms of viscosity stability, to pH extremes than a similar EHEC polymer, particularly at the high pH range.

Example 10

Shampoo Stability of Formulations Containing EHEC and MEHEC Polymers

Shampoos containing EHEC and MEHEC were prepared and the corresponding viscosities measured using the following procedure:

1. 765.0 g water was added to a 2000 mL beaker and was mixed using a Jiffy blade on an overhead mixer, making sure to pull a vortex (about 400-500 rpm).
2. Sodium Lauryl Ether Sulfate (STANDAPOL® ES-2, available from BASF, Ludwigshafen, Germany) and Cocamidopropyl Betaine (Crodateric™ CAB 30, available from Croda Inc., Edison, N.J.) were added to the vessel and allowed to mix until homogeneous.
3. Slowly sift in the STRUCTURE® CEL polymer over 1 to 2 minutes and began heating the solution to 40-45° C.
4. When the viscosity has increased (about 20-30 minutes), the heat was turned off and the mixing was reduced to 200-300 rpm until the mixture had cooled to room temperature (about 25° C.)
5. Once cooled, the remaining ingredients were added to the batch and the viscosity was measured using the procedure as described in step 3 of example XXX.

TABLE 13

Shampoo viscosity with EHEC and MEHEC

| Raw Material Name | 68 | 1000 g | 89 | 1000 g |
|---|---|---|---|---|
| Deionized Water | 76.50% | 765.00 | 76.50% | 765.00 |
| STANDAPOL ® ES-2 (25% active) | 15.00% | 150.00 | 15.00% | 150.00 |
| Crodateric ™ CAB 30 (30% active) | 5.00% | 50.00 | 5.00% | 5.00 |
| STRUCTURE ® CEL 4400 E rheology modifier (EHEC) | | | 1.00% | 10.00 |
| STRUCTURE ® CEL 8000 M rheology modifier (MEHEC) | 1.00% | 10.00 | | |
| Euperlan ® PK3000 AM | 2.00% | 20.00 | 2.00% | 20.00 |
| Glydant ™ Plus (liquid) | 0.50% | 5.00 | 0.50% | 5.00 |
| Initial pH | 6.32 | | 6.37 | |
| Viscosity (RVT-C @ 10 rpm), initial | 7800 cps | | 5640 cps | |
| Viscosity (RVT-C @ 10 rpm), 12 weeks @ 45° C. | 6680 cps | | 2000 cps | |
| % Loss | 14.36% | | 64.54% | |

The EHEC-based formula (STRUCTURE® CEL 4400 E rheology modifier) exhibited considerable loss in viscosity and also displayed some settling of the pearlizer (Eurperlan® PK 3000 AM, glycol distearate and cocamidopropyl betaine available from BASF Corporation, Ambler, Pa.)) onto the bottom of the sample jars. The same formula but utilizing MEHEC (STRUCTURE® CEL 8000 M rheology modifier) had no settling and maintained its viscosity throughout the entire stability.

TABLE 14

Shampoo viscosity stability over time

| Formula/ temperature | Viscosity (RVT-C, 10 rpm, 100 g sample, 4 oz tall jar, 2 minutes) | | | | | |
|---|---|---|---|---|---|---|
| | Initial | Week 1 | Week 2 | Week 4 | Week 8 | Week 12 |
| 68/4 C. | 7800 | 7400 | 7600 | 7500 | 7700 | 8860 |
| 68/RT | 7800 | 7300 | 7400 | 7100 | 7260 | 7280 |
| 68/45° C. | 7800 | 6600 | 6600 | 5400 | 5020 | 6680 |
| 89/4 C. | 5720 | 5760 | 5920 | 5700 | 5600 | 5640 |
| 89/RT | 5660 | 5580 | 5740 | 5480 | 5260 | 5200 |
| 89/45° C. | 5640 | 5060 | 4420 | 3240 | 2480 | 2000 |

While both formulas show some decline at 45° C., the 8000 M formula exhibits a much lower loss and also eventually recovers some of the loss after 12 weeks. This is not noted in the 4400 E formula.

Although the invention is illustrated and described herein with reference to specific embodiments, the invention is not intended to be limited to the details shown. Rather, various modifications may be made in the details within the scope and range of equivalents of the claims and without departing from the spirit of the invention.

What is claimed is:

1. A personal care formulation comprising:
   methyl ethyl hydroxyethyl cellulose having a methyl DS to ethyl DS ratio of from about 1 to about 6.5; and
   at least one cosmetically acceptable ingredient,
   wherein the weight average molecular weight of the methyl ethyl hydroxyethyl cellulose is from about 100,000 to about 3,000,000 Da.

2. The formulation of claim 1, wherein the methyl ethyl hydroxyethyl cellulose has a methyl DS to ethyl DS ratio of from about 1.0 to about 3.0.

3. The formulation of claim 2 wherein the methyl ethyl hydroxyethyl cellulose has a methyl DS to ethyl DS ratio of from about 1.2 to about 3.0.

4. The formulation of claim 3 wherein the methyl ethyl hydroxyethyl cellulose has a methyl DS to ethyl DS ratio of amount of from about 2.0 to about 3.0.

5. A personal care formulation comprising:
   methyl ethyl hydroxyethyl cellulose having a methyl DS to ethyl DS ratio of from about 1 to about 6.5; and
   at least one cosmetically acceptable ingredient,
   wherein the weight average molecular weight of the methyl ethyl hydroxyethyl cellulose is about 1,000,000 Da or greater.

6. A personal care formulation comprising:
   methyl ethyl hydroxyethyl cellulose having a methyl DS to ethyl DS ratio of from about 1 to about 6.5; and
   at least one cosmetically acceptable ingredient,
   wherein the methyl ethyl hydroxyethyl cellulose further contains a cationic substituent.

7. The formulation of claim 1 further comprising a cleanser.

8. The formulation of claim 1 wherein the formulation is substantially sulfate free.

9. The formulation of claim 7 wherein the formulation is a shampoo.

10. A hair gel comprising a personal care formulation comprising methyl ethyl hydroxyethyl cellulose having a methyl DS to ethyl DS ratio of from about 1 to about 6.5; and at least one cosmetically acceptable ingredient and further comprising a styling polymer.

11. The hair gel formulation of claim 10 wherein the styling polymer is selected from the group consisting of polyvinyl pyrrolidinone, polyvinyl pyrrolidinone copolymers, polyvinyl formamide, polyvinyl acetamide, and mixtures thereof.

12. The formulation of claim 1 wherein the formulation further comprises an anionic surfactant.

13. A method of thickening a personal care composition comprising adding a methyl ethyl hydroxyethyl cellulose having a methyl DS to ethyl DS ratio of from 1 to 6.5 wherein the composition further comprises at least one cosmetically acceptable ingredient and wherein the weight average molecular weight of the methyl ethyl hydroxyethyl cellulose is from 100,000 to 3,000,000 Da.

14. A method of thickening a personal care composition comprising adding a methyl ethyl hydroxyethyl cellulose having a methyl DS to ethyl DS ratio of from 1 to 6.5 wherein the composition further comprises at least one cosmetically acceptable ingredient, and wherein the weight average molecular weight of the methyl ethyl hydroxyethyl cellulose is 1,000,000 Da or greater.

15. The formulation of claim 1, wherein the weight average molecular weight of the methyl ethyl hydroxyethyl cellulose is from about 500,000 to about 2,000,000 Da.

16. The formulation of claim 5, wherein the weight average molecular weight of the methyl ethyl hydroxyethyl cellulose is about 1,300,000 Da or greater.

17. The hair gel formulation of claim 10 wherein the hair gel has a high humidity curl retention of about 20 percent or greater at 24 hours and 90% RH when compared to a hair gel having ethyl hydroxyethylcellulose.

18. The formulation of claim 5, wherein the methyl ethyl hydroxyethyl cellulose has a methyl DS to ethyl DS ratio of from about 1.0 to about 3.0.

19. The formulation of claim 18 wherein the methyl ethyl hydroxyethyl cellulose has a methyl DS to ethyl DS ratio of from about 1.2 to about 3.0.

20. The formulation of claim 19 wherein the methyl ethyl hydroxyethyl cellulose has a methyl DS to ethyl DS ratio of from about 2.0 to about 3.0.

21. The formulation of claim 6 further comprising a cleanser.

22. The formulation of claim 6 wherein the formulation is substantially sulfate free.

23. The formulation of claim 22 wherein the formulation is a shampoo.

* * * * *